US012586676B2

(12) United States Patent
Reicher et al.

(10) Patent No.: US 12,586,676 B2
(45) Date of Patent: Mar. 24, 2026

(54) IMAGE INTERPRETATION MODEL DEVELOPMENT

(71) Applicant: Synthesis Health Inc., Vancouver (CA)

(72) Inventors: Murray Aaron Reicher, Rancho Santa Fe, CA (US); Deepak Kaura, Calgary (CA)

(73) Assignee: Synthesis Health Inc., Maple Ridge (CA)

( * ) Notice: Subject to any disclaimer, the term of this patent is extended or adjusted under 35 U.S.C. 154(b) by 41 days.

(21) Appl. No.: 18/493,650

(22) Filed: Oct. 24, 2023

(65) Prior Publication Data

US 2025/0078987 A1     Mar. 6, 2025

Related U.S. Application Data

(60) Provisional application No. 63/535,868, filed on Aug. 31, 2023.

(51) Int. Cl.
G16H 30/40          (2018.01)
G06F 40/40          (2020.01)
(Continued)

(52) U.S. Cl.
CPC ............. G16H 30/40 (2018.01); G06F 40/40 (2020.01); G16H 15/00 (2018.01); G16H 30/20 (2018.01); G16H 50/20 (2018.01); G16H 50/70 (2018.01)

(58) Field of Classification Search
None
See application file for complete search history.

(56) References Cited

U.S. PATENT DOCUMENTS 7,646,898 B1     1/2010  Nowinski et al.
10,210,310 B2    2/2019  Carolus et al.
(Continued)

FOREIGN PATENT DOCUMENTS

CN        112309528      2/2021
CN        115035089      9/2022
(Continued)

OTHER PUBLICATIONS

Sugimoto et al.: "Extracting clinical terms from radiology reports with deep learning"; Mar. 9, 2021 (Year: 2021).*
(Continued)

*Primary Examiner* — John A Pauls
(74) *Attorney, Agent, or Firm* — Knobbe, Martens, Olson & Bear, LLP

(57) ABSTRACT

An image classification model, e.g., a neural network model, may be trained on a set of training medical imaging exams each including a training report and a training medical image. A model generation module or device may, for each of the training medical imaging exams: use finding item criteria to reorganize text of the training report into a list of finding items, each associated with text extracted from the training report text, use natural language processing to analyze the resultant text associated with each finding item to determine an associated classification of each finding item, store, in a training dataset, the training medical imaging exam, the associated finding items, the matching text, and the classifications resulting from the analysis of the matching text. The trained neural network learns to output, for other medical imaging exams, one or more finding items and an associated classification data.

16 Claims, 10 Drawing Sheets

(51) Int. Cl.

| | |
|---|---|
| *G16H 15/00* | (2018.01) |
| *G16H 30/20* | (2018.01) |
| *G16H 50/20* | (2018.01) |
| *G16H 50/70* | (2018.01) |

(56) References Cited

U.S. PATENT DOCUMENTS

| | | | |
|---|---|---|---|
| 10,580,528 | B2 | 3/2020 | McLaughlin et al. |
| 11,263,749 | B1 | 3/2022 | Purushottam et al. |
| 11,540,794 | B2 | 1/2023 | Boddington et al. |
| 2008/0146923 | A1 | 6/2008 | Mejla et al. |
| 2008/0205721 | A1 | 8/2008 | Udupa et al. |
| 2009/0092300 | A1 | 4/2009 | Jerebko et al. |
| 2010/0095340 | A1 | 4/2010 | Ei et al. |
| 2013/0251233 | A1 | 9/2013 | Yang et al. |
| 2014/0115020 | A1 | 4/2014 | Colaco et al. |
| 2016/0121142 | A1 | 5/2016 | Zhang et al. |
| 2016/0154933 | A1 | 6/2016 | Ramanathan |
| 2017/0069084 | A1* | 3/2017 | Kubo ..................... A61B 6/469 |
| 2018/0326149 | A1 | 11/2018 | Lipschultz et al. |
| 2019/0042703 | A1 | 2/2019 | Reicher et al. |
| 2019/0096060 | A1 | 3/2019 | Zhang et al. |
| 2019/0139218 | A1* | 5/2019 | Song ........................ G06N 3/08 |
| 2019/0139238 | A1 | 5/2019 | Wyeth |
| 2019/0171714 | A1* | 6/2019 | Gale ...................... G16H 40/20 |
| 2019/0188870 | A1 | 6/2019 | Park et al. |
| 2019/0237184 | A1 | 8/2019 | Sharma et al. |
| 2019/0290215 | A1 | 9/2019 | Gilbert |
| 2019/0325249 | A1 | 10/2019 | Maraghoosh et al. |
| 2020/0043600 | A1 | 2/2020 | Glottmann et al. |
| 2020/0178794 | A1 | 6/2020 | El-Baz et al. |
| 2020/0321100 | A1 | 10/2020 | Glottmann et al. |
| 2021/0020303 | A1 | 1/2021 | Accomazzi et al. |
| 2021/0065859 | A1 | 3/2021 | McKinney et al. |
| 2021/0134465 | A1 | 5/2021 | Gooßen et al. |
| 2021/0216822 | A1 | 7/2021 | Paik et al. |
| 2021/0264212 | A1 | 8/2021 | Paik et al. |
| 2021/0282730 | A1 | 9/2021 | Singh et al. |
| 2021/0375435 | A1 | 12/2021 | O'Connor et al. |
| 2022/0037019 | A1 | 2/2022 | Covington et al. |
| 2022/0084209 | A1 | 3/2022 | Wang et al. |
| 2022/0265233 | A1 | 8/2022 | Boddington et al. |
| 2023/0070444 | A1 | 3/2023 | Kartmann et al. |
| 2023/0108955 | A1 | 4/2023 | Weissman et al. |
| 2023/0334663 | A1 | 10/2023 | Reicher |
| 2023/0334763 | A1 | 10/2023 | Reicher |
| 2023/0335261 | A1 | 10/2023 | Reicher et al. |
| 2024/0087724 | A1 | 3/2024 | Sawarkar et al. |
| 2024/0153094 | A1 | 5/2024 | Liu et al. |
| 2024/0331354 | A1 | 10/2024 | Azad et al. |
| 2025/0078970 | A1 | 3/2025 | Reicher et al. |

FOREIGN PATENT DOCUMENTS

| | | |
|---|---|---|
| EP | 2561458 | 7/2021 |
| JP | 2020-523711 | 8/2020 |
| KR | 10-2018-0040287 | 4/2018 |
| KR | 10-2019-0102399 | 9/2019 |
| KR | 10-2374278 | 3/2022 |
| WO | WO 2014/085918 | 6/2014 |
| WO | WO 2020/8026033 | 2/2020 |
| WO | WO 2022/144360 | 7/2022 |
| WO | WO 2023/205177 | 10/2023 |
| WO | WO 2023/205179 | 10/2023 |
| WO | WO 2023/205181 | 10/2023 |
| WO | WO 2024/102765 | 5/2024 |
| WO | WO 2024/102832 | 5/2024 |
| WO | WO 2025/048865 | 3/2025 |
| WO | WO 2025/155564 | 7/2025 |

OTHER PUBLICATIONS

International Search Report and Written Opinion for International Application No. PCT/US2023/018991 dated Aug. 8, 2023; 10 pages.

International Search Report and Written Opinion for International Application No. PCT/US2023/018985 dated Aug. 16, 2023; 10 pages.

International Search Report and Written Opinion for International Application No. PCT/US2023/018987 dated Aug. 1, 2023; 11 pages.

International Search Report and Written Opinion for International Application No. PCT/US2023/079001 dated Feb. 29, 2024; 11 pages.

International Search Report and Written Opinion for International Application No. PCT/US2023/079117 dated Mar. 6, 2024; 12 pages.

International Search Report and Written Opinion for International Application No. PCT/US2023/078010 dated May 20, 2024; 8 pages.

International Search Report and Written Opinion for International Application No. PCT/US2025/011591 dated Jul. 2, 2025, 10 pages.

* cited by examiner

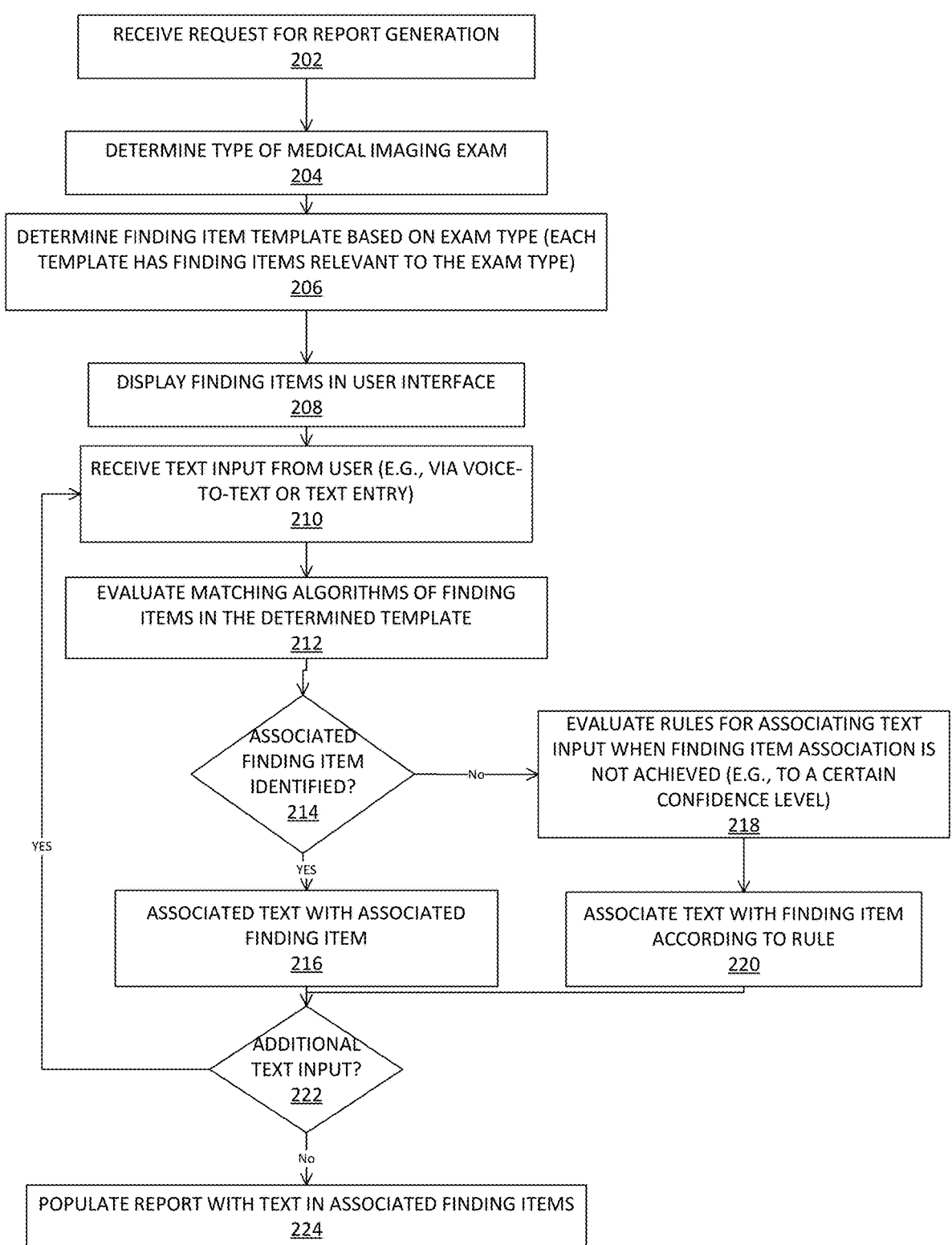

RECEIVE REQUEST FOR REPORT GENERATION
202

DETERMINE TYPE OF MEDICAL IMAGING EXAM
204

DETERMINE FINDING ITEM TEMPLATE BASED ON EXAM TYPE (EACH
TEMPLATE HAS FINDING ITEMS RELEVANT TO THE EXAM TYPE)
206

DISPLAY FINDING ITEMS IN USER INTERFACE
208

RECEIVE TEXT INPUT FROM USER (E.G., VIA VOICE-
TO-TEXT OR TEXT ENTRY)
210

EVALUATE MATCHING ALGORITHMS OF FINDING
ITEMS IN THE DETERMINED TEMPLATE
212

ASSOCIATED
FINDING ITEM
IDENTIFIED?
214

EVALUATE RULES FOR ASSOCIATING TEXT
INPUT WHEN FINDING ITEM ASSOCIATION IS
NOT ACHIEVED (E.G., TO A CERTAIN
CONFIDENCE LEVEL)
218

No

YES

ASSOCIATED TEXT WITH ASSOCIATED
FINDING ITEM
216

ASSOCIATE TEXT WITH FINDING ITEM
ACCORDING TO RULE
220

YES

ADDITIONAL
TEXT INPUT?
222

No

POPULATE REPORT WITH TEXT IN ASSOCIATED FINDING ITEMS
224

FIG. 2

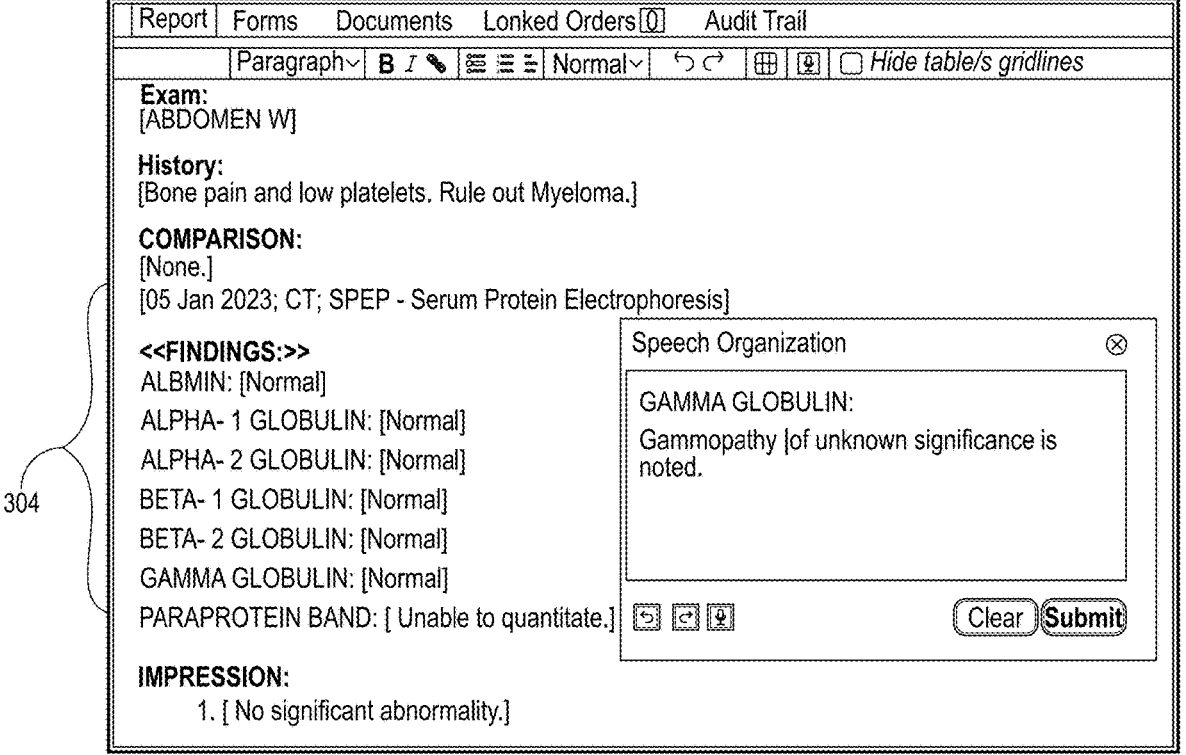

| Report | Forms     Documents     Lonked Orders[0]     Audit Trail |

Paragraph⌄ | B *I* ✎ | ☰ ☰ ☰ | Normal⌄ | ↺ ↻ | ⊞ | ▣ | ☐ *Hide table/s gridlines*

Exam:
[ABDOMEN W]

History:
[Bone pain and low platelets. Rule out Myeloma.]

COMPARISON:
[None.]
[05 Jan 2023; CT; SPEP - Serum Protein Electrophoresis]

<<FINDINGS:>>
ALBMIN: [Normal]

ALPHA- 1 GLOBULIN: [Normal]

ALPHA- 2 GLOBULIN: [Normal]

BETA- 1 GLOBULIN: [Normal]

BETA- 2 GLOBULIN: [Normal]

GAMMA GLOBULIN: [Normal]

PARAPROTEIN BAND: [ Unable to quantitate.]

IMPRESSION:
    1. [ No significant abnormality.]

304

Speech Organization                                    ⊗

GAMMA GLOBULIN:

Gammopathy [of unknown significance is noted.

↺ ↻ ▣                          ( Clear )( Submit )

FIG. 3B

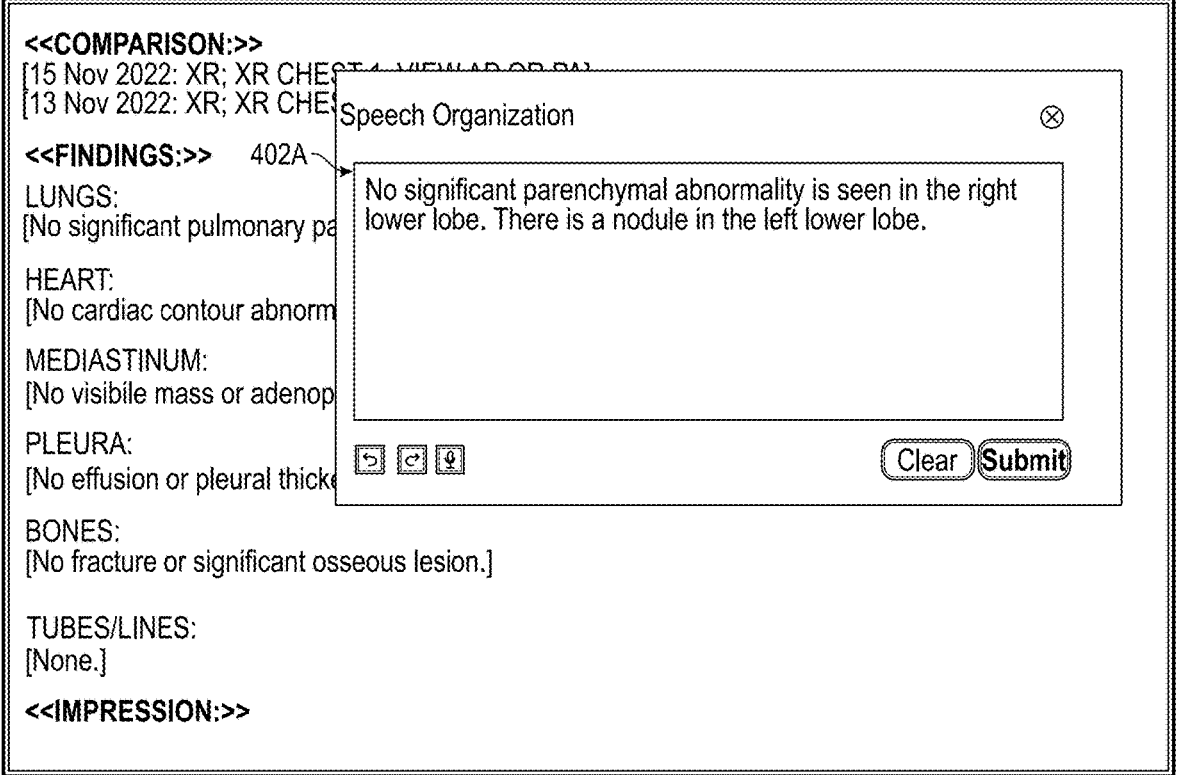

<<COMPARISON:>>
[15 Nov 2022: XR; XR CHEST 1 VIEW AP OR PA]
[13 Nov 2022: XR; XR CHE

Speech Organization          ⊗

<<FINDINGS:>>   402A

No significant parenchymal abnormality is seen in the right lower lobe. There is a nodule in the left lower lobe.

LUNGS:
[No significant pulmonary pa

HEART:
[No cardiac contour abnorm

MEDIASTINUM:
[No visibile mass or adenop

PLEURA:
[No effusion or pleural thick

⤺ ⤻ ⬇          Clear  Submit

BONES:
[No fracture or significant osseous lesion.]

TUBES/LINES:
[None.]

<<IMPRESSION:>>

FIG. 4

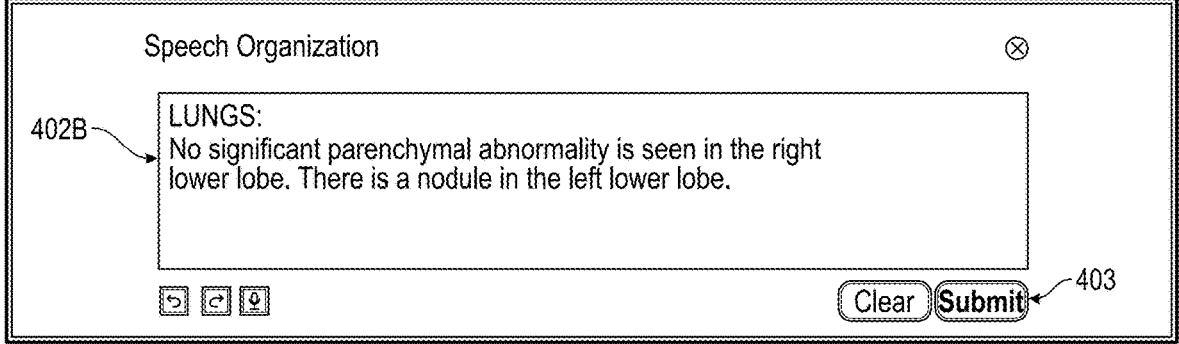
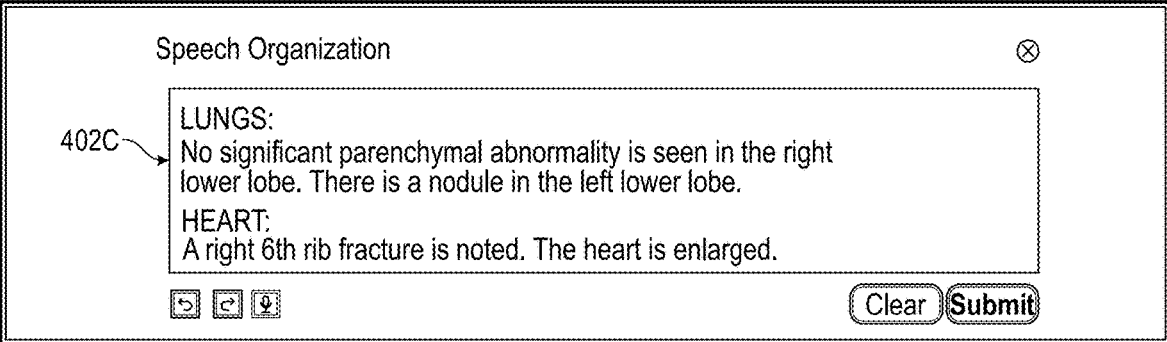
FIG. 4
(Continued)

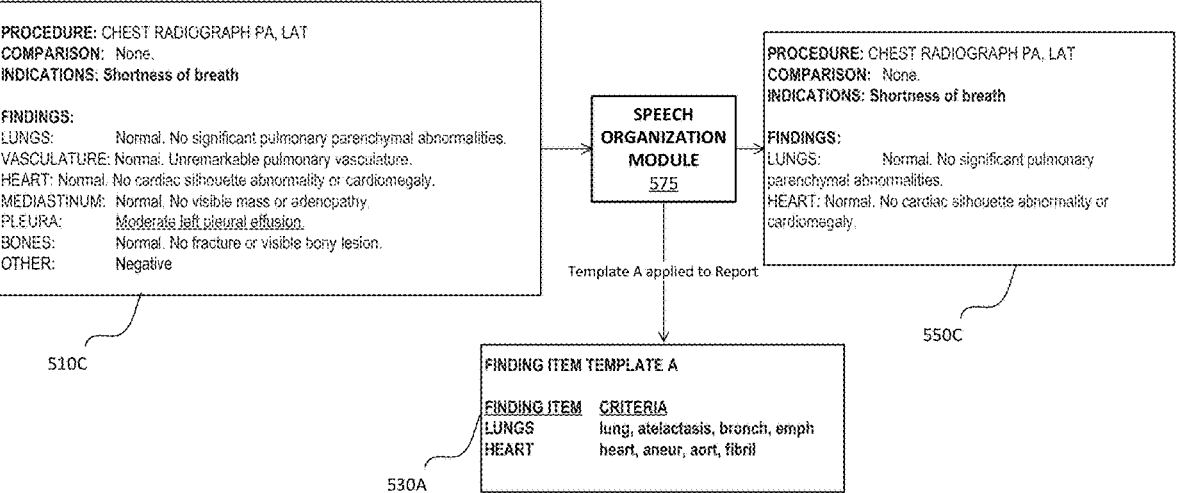

PROCEDURE: CHEST RADIOGRAPH PA, LAT
COMPARISON:  None.
INDICATIONS: Shortness of breath FINDINGS:
LUNGS:        Normal. No significant pulmonary parenchymal abnormalities.
VASCULATURE: Normal. Unremarkable pulmonary vasculature.
HEART: Normal. No cardiac silhouette abnormality or cardiomegaly.
MEDIASTINUM: Normal. No visible mass or adenopathy.
PLEURA:       Moderate left pleural effusion.
BONES:        Normal. No fracture or visible bony lesion.
OTHER:        Negative

510C

SPEECH
ORGANIZATION
MODULE
575

Template A applied to Report

PROCEDURE: CHEST RADIOGRAPH PA, LAT
COMPARISON:  None.
INDICATIONS: Shortness of breath FINDINGS:
LUNGS:        Normal. No significant pulmonary
parenchymal abnormalities.
HEART: Normal. No cardiac silhouette abnormality or
cardiomegaly.

550C

FINDING ITEM TEMPLATE A

FINDING ITEM   CRITERIA
LUNGS          lung, atelactasis, bronch, emph
HEART          heart, aneur, aort, fibril

IMAGE INTERPRETATION MODEL DEVELOPMENT

BACKGROUND

AI algorithm development for medical imaging often requires expensive, time-consuming, manual annotation of medical imaging findings. For example, a radiologist may be required to view medical images and indicate whether specific findings are present or not, and where the findings are located.

SUMMARY

The systems, methods, and devices described herein each have several aspects, no single one of which is solely responsible for its desirable attributes. Without limiting the scope of this disclosure, several non-limiting features will now be described briefly.

Disclosed herein are systems and methods to generate image interpretation models (such as neural network models) for analysis of medical images without requiring manual image annotation. In some embodiments, an image interpretation model is trained using a training dataset that includes medical images with associated text reports, wherein the text reports have been processed using a speech organization module, such as is described in U.S. Provisional Application No. 63/535,868, titled "Speech Organization In Medical Imaging Examination Reports," to which this application claims priority and which is hereby incorporated by reference in its entirety. In some embodiments, after the reports are organized into one or more finding items with associated text content ("finding item text"), one or more of the findings items and associated finding item text is automatically analyzed using a natural language processing engine. Such analysis may classify the finding, such as positive vs. negative, improved vs. worse, observation vs. recommendation, or even more specific classifications such as tumor vs. infection vs. auto-immune disease, or fracture vs. other bone lesion. These classifications of finding item texts (or "indications") may then be used, in association with the corresponding report and medical image, as a training data set to train an image interpretation model that may classify medical images without requiring manual annotation.

For example, an image interpretation model (e.g., a neural network model or other artificial intelligence model) may be used to analyze other images, e.g., medical images that have not been read by a radiologist, to determine predicted finding item indications (e.g., whether or not the image indicates a finding for a particular finding item) that may be used to generate a medical report, to diagnosis a patient, and/or to treat a patient, such as in near real-time to acquisition of the image via imaging equipment.

In some implementations, a human expert may review and correct the results of the speech organization and/or natural language processing engine to improve the accuracy of the annotation prior to training the image interpretation model.

In some implementations, the image interpretation model may be used to create annotations for other medical images, then a human expert may review and correct the results, and the corrected results may be used to train or retrain an image interpretation model.

In some implementations, a training dataset is selected to include a relevant set of medical exams (e.g., medical reports and associated medical images), such as medical reports that were generated by a particular user or group of users, type of medical images, medical imaging modality, report findings, etc. Thus, in some implementations an image classification model may be created based on reports from well-reputed readers. These specialized models may be used to simulate finding item identification and/or reporting styles of those well-reputed users. Further, such specialized models may be licensed or sold without requiring any prospective manual annotation by a reader.

In some implementations, the image interpretation model may be used to perform retrospective quality analysis of medical imaging reports to help train physicians, assess malpractice risk, rate or improve quality. The quality analysis may be used by a medical professional service business as a competitive advantage in promoting its business. It may become part of a quality metric that is used to reward participating practitioners or institutions.

The following description discusses various processes and components that may perform artificial intelligence ("AI") processing or functionality. AI generally refers to the field of creating computer systems that can perform tasks that typically require human intelligence. This includes understanding natural language, recognizing objects in images, making decisions, and solving complex problems. AI systems can be built using various techniques, like neural networks, rule-based systems, or decision trees, for example. Neural networks learn from vast amounts of data and can improve their performance over time. Neural networks may be particularly effective in tasks that involve pattern recognition, such as image recognition, speech recognition, or Natural Language Processing.

Natural Language Processing (NLP) is an area of artificial intelligence (AI) that focuses on teaching computers to understand, interpret, and generate human language. By combining techniques from computer science, machine learning, and/or linguistics, NLP allows for more intuitive and user-friendly communication with computers. NLP may perform a variety of functions, such as sentiment analysis, which determines the emotional tone of text; machine translation, which automatically translates text from one language or format to another; entity recognition, which identifies and categorizes things like people, organizations, or locations within text; text summarization, which creates a summary of a piece of text; speech recognition, which converts spoken language into written text; question-answering, which provides accurate and relevant answers to user queries, and/or other related functions. Natural Language Understanding (NLU), as used herein, is a type of NLP that focuses on the comprehension aspect of human language. NLU may attempt to better understand the meaning and context of the text, including idioms, metaphors, and other linguistic nuances.

A Language Model is any algorithm, rule, model, and/or other programmatic instructions that can predict the probability of a sequence of words. A language model may, given a starting text string (e.g., one or more words), predict the next word in the sequence. A language model may calculate the probability of different word combinations based on the patterns learned during training (based on a set of text data from books, articles, websites, audio files, etc.). A language model may generate many combinations of one or more next words (and/or sentences) that are coherent and contextually relevant. Thus, a language model can be an advanced artificial intelligence algorithm that has been trained to understand, generate, and manipulate language. A language model can be useful for natural language processing, including receiving natural language prompts and providing natural language responses based on the text on which the model is trained. A language model may include an n-gram, exponential, positional, neural network, and/or other type of model.

A Large Language Model ("LLM") is any type of language model that has been trained on a larger data set and has a larger number of training parameters compared to a regular language model. An LLM can understand more intricate patterns and generate text that is more coherent and contextually relevant due to its extensive training. Thus, an LLM may perform well on a wide range of topics and tasks. An LLM may comprise a NN trained using self-supervised learning. An LLM may be of any type, including a Question Answer ("QA") LLM that may be optimized for generating answers from a context, a multimodel LLM/model, and/or the like. An LLM (and/or other models of the present disclosure), may include, for example, attention-based and/or transformer architecture or functionality. LLMs can be extremely useful for natural language processing, including receiving natural language prompts and providing natural language responses based on the text on which the model is trained.

As used herein, references to specific uses and/or implementations of AI, NLP, NLU, or LLM should be interpreted to include any other implementations, including any of those discussed above. For example, references to NLP herein should be interpreted to include NLU also.

A system of one or more computers can be configured to perform the below example operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 2 is a flowchart illustrating an example process for generating a report using templates with finding items (or "finding item templates").

FIG. 3B illustrates an example user interface of a laboratory report for a clinical chemistry workflow.

FIG. 4 illustrates another example user interface that may be displayed responsive to the user selecting a voice to text function.

in medical images based on training data that has been organized using the speech organization systems and methods discussed above.

Figure 7:
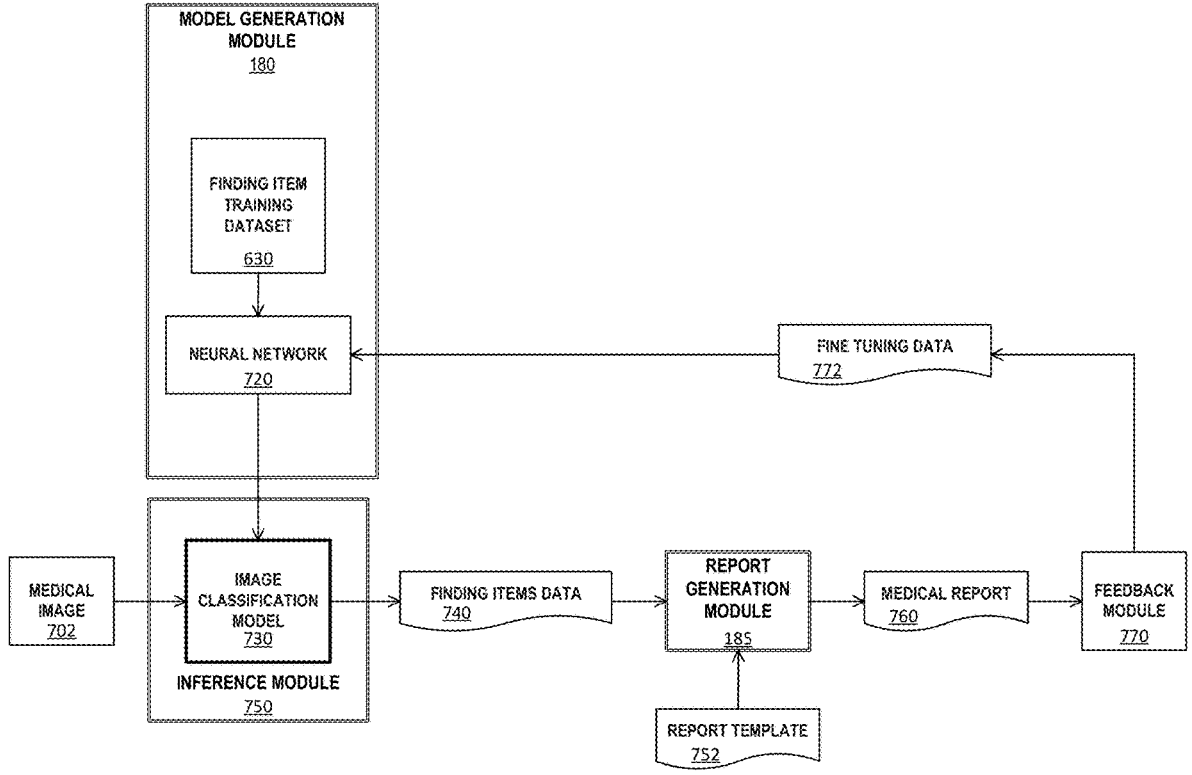

FIG. 7 is a block diagram illustrating a neural network that is trained using a trained data set, and which outputs an image classification model that is usable by an inference module.

DETAILED DESCRIPTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with certain specific embodiments. Furthermore, embodiments of the invention may include several novel features, no single one of which is solely responsible for its desirable attributes or which is essential to practicing the inventions herein described.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
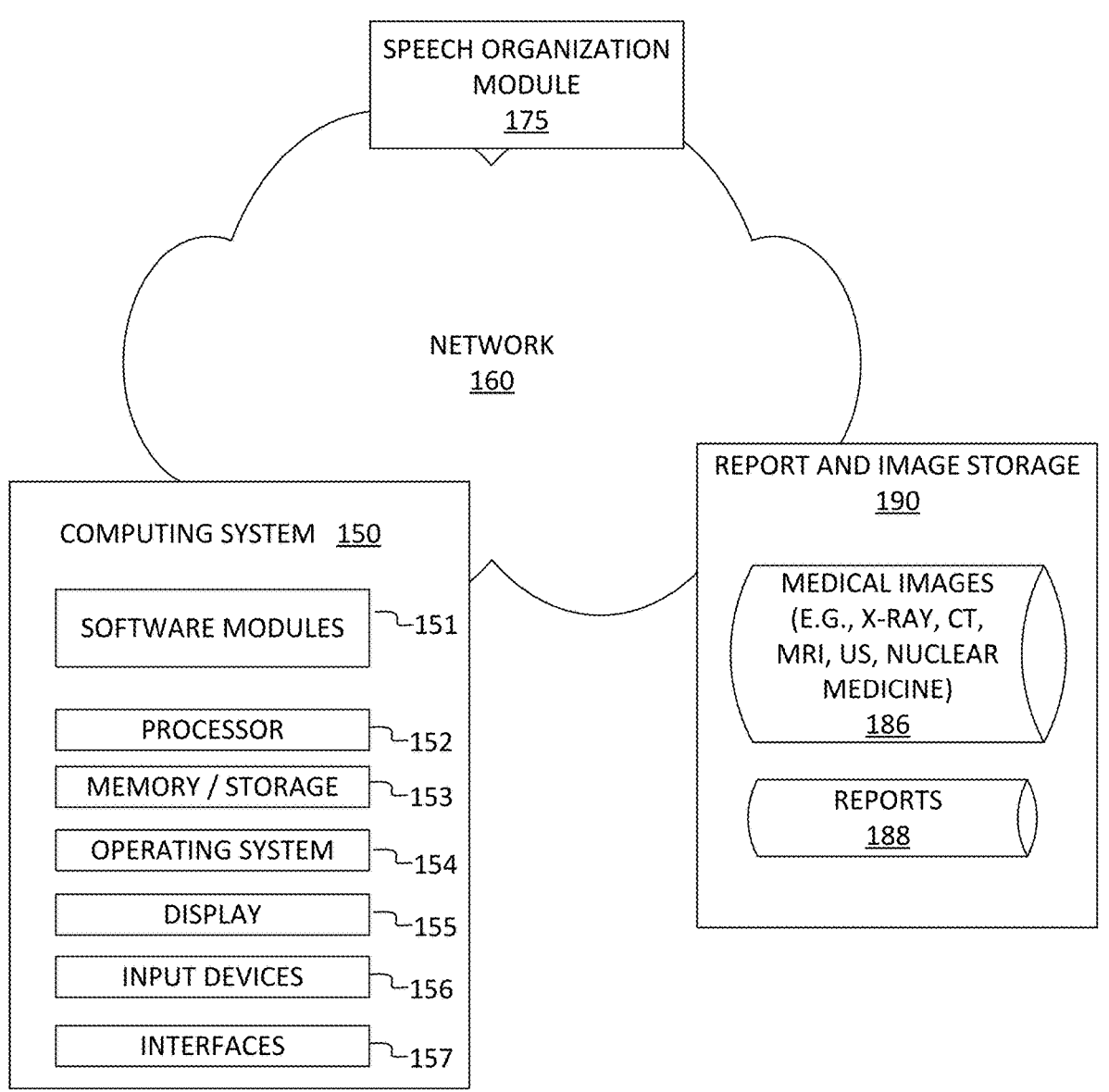
FIG. 1 illustrates an example computing system.

The systems and methods discussed herein may be performed by various computing systems, which are referred to herein generally as a viewing device or computing system (such as computing system 150 of FIG. 1). A computing system may include, for example, a picture archiving and communication system ("PACs") or other computing system configured to display images, such as computed tomography ("CT"), magnetic resonance imaging ("MRI"), ultrasound ("US"), radiography ("XR"), positron emission tomography ("PET"), nuclear medicine ("NM"), fluoroscopy ("FL"), photographs, and/or any other type of image. Any of the computer processing discussed herein, such as application of artificial intelligence ("AI") and/or development or updating of AI algorithms, may be performed at the computing system and/or at one or more backend or cloud devices, such as one or more servers. Thus, even if a particular computerized processes is described herein as being performed by a particular computing system (e.g., a PACS or sever), the processes may be performed partially or fully by other devices.

Example System

FIG. 1 illustrates an example computing system 150 (also referred to herein as a "computing device 150" or "system 150"). The computing system 150 may take various forms. In one embodiment, the computing system 150 may be a computer workstation having modules 151, such as software, firmware, and/or hardware modules. In other embodiments, modules 151 may reside on another computing device, such as a web server, and the user directly interacts with a second computing device that is connected to the web server via a computer network.

In various embodiments, the computing system 150 comprises one or more of a server, a desktop computer, a workstation, a laptop computer, a mobile computer, a Smartphone, a tablet computer, a cell phone, a personal digital assistant, a gaming system, a kiosk, any other device that utilizes a graphical user interface, including office equipment, automobiles, industrial equipment, and/or a television, for example. In one embodiment, for example, the computing system 150 comprises a tablet computer that provides a user interface responsive to contact with a human hand/finger or stylus.

The computing system 150 may run an off-the-shelf operating system 154 such as a Windows, Linux, MacOS, Android, IOS, or other. The computing system 150 may also run a more specialized operating system which may be designed for the specific tasks performed by the computing system 150.

The computing system 150 may include one or more hardware computing processors 152. The computer processors 152 may include central processing units (CPUs) and may further include dedicated processors such as graphics processor chips, or other specialized processors. The processors generally are used to execute computer instructions based on the software modules 151 to cause the computing device to perform operations as specified by the modules 151.

The various software modules 151 (or simply "modules 151") may be provided on a computer readable medium, such as a compact disc, digital video disc, flash drive, or any other tangible medium. Such software code may be stored, partially or fully, on a memory device of the executing computing device for execution by the computing device. The application modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The computing system 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The computing system 150 may also include or be interfaced to one or more display devices 155 that provide information to the users. A display device 155 may provide for the presentation of GUIs, application software data, and multimedia presentations, for example. Display devices 155 may include a video display, such as one or more high-resolution computer monitors, or a display device integrated into or attached to a laptop computer, handheld computer, Smartphone, computer tablet device, or medical scanner. In other embodiments, the display device 155 may include an LCD, OLED, or other thin screen display surface, a monitor, television, projector, a display integrated into wearable glasses, such as a virtual reality or augmented reality headset, or any other device that visually depicts user interfaces and data to viewers.

The computing system 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The computing system 150 may also include one or more interfaces 157 which allow information exchange between computing system 150 and other computers and input/output devices using systems such as Ethernet, Wi-Fi, Bluetooth, as well as other wired and wireless data communications techniques.

The modules of the computing system 150 may be connected using a standard based bus system. The functionality provided for in the components and modules of computing system 150 may be combined into fewer components and modules or further separated into additional components and modules.

In the example of FIG. 1, the computing system 150 is connected to a computer network 160, which allows communications with various other devices, both local and remote. The computer network 160 may take various forms. It may be a wired network or a wireless network, or it may be some combination of both. The computer network 160 may be a single computer network, or it may be a combination or collection of different networks and network protocols. For example, the computer network 160 may include one or more local area networks (LAN), wide area networks (WAN), personal area networks (PAN), cellular or data networks, and/or the Internet.

Various devices and subsystems may be connected to the network 160. For example, one or more medical imaging device that generate images associated with a patient in various formats, such as Computed Tomography ("CT"), magnetic resonance imaging ("MRI"), Ultrasound ("US"), (X-Ray) ("XR"), Positron emission tomography ("PET"), Nuclear Medicine ("NM"), Fluoroscopy ("FL"), photographs, illustrations and/or any other type of image. These devices may be used to acquire such medical images 186 from patients, and may share the acquired images with other devices on the network 160. Medical images may be stored in any format, such as an open source format or a proprietary format. A common format for image storage in the PACS system is the Digital Imaging and Communications in Medicine (DICOM) format.

In the example of FIG. 1, a report and image storage 190 stores various modalities of medical images 186 and medical reports 188. In an example implementation, when a new medical image acquired via medical imaging equipment, is stored in the medical images 186 an image segmentation and analysis process is initiated. In some embodiments, the computing system 150 may be notified of the available image and initiate automatic segmentation and/or analysis of the medical image.

Example Text Categorization Using Finding Item Templates

In the example of FIG. 1, the computing system 150 is configured to execute a Speech Organization module 175. In some embodiments, the Speech Organization module 175 is stored partially or fully in the software modules 151 of the system 150. In some implementations, the Speech Organization module 175 may be stored remote from the computing system 150, such as on another device that is accessible via a local or wide area network (e.g., via network 160). For example, the speech organization module 175 may operate in the cloud (e.g., on a server connected to the Internet), in communication with the computing system 150, which displays the various user interfaces to the user and interacts with user. In such an embodiment, any number of user devices may communicate with and make use of the speech organization module 175 with little or no software installation required on their mobile computing device (e.g., a browser-based user interface may be implemented in some examples). In an example implementation, the Speech Organization module 175 parses input text (receive via voice or other input device) and associates the text with appropriate finding items of a medical report.

FIG. 2 is a flowchart illustrating an example process for generating a report using templates with finding items (or "finding item templates"). Depending on the implementation, the method may include fewer or additional blocks and/or the blocks may be performed in an order different than illustrated.

Beginning at block 202, a request for report generation is received, such as by the computing system 150. For example, a user of the system 150 may select an imaging exam for review, e.g., a newly received imaging exam that the user is tasked with reviewing and generating a report on. In other examples, the request for report generation may be obtained in other manners.

Next, at block 204 a type of the medical imaging exam is determined. For example, the type of exam may be determined based on metadata (e.g., DICOM data) associated with the medical imaging exam. In some embodiments, the user may select a type of imaging exam, such as from a user interface that displays the most likely or most frequently used imaging exam types (e.g., associated with the user). In some examples, a "type" of the medical imaging exam could be any characteristic associated with the medical imaging exam.

At block 206, a finding item template associated with the exam type is determined or is manually selected. In some implementations a finding item template is part of, or is determined based on, a report template (e.g., an outline of a report with finding items associated with a particular exam type and/or attribute, and possibly with default report text for some or all of the finding items). For example, in one example, a report template associated with an exam may be selected and then finding item criteria for each of the finding items in the report template are determined for use in identifying additional finding item text to be associated with respective finding items, as discussed below. The set of finding item criteria (and related finding items) associated with a report may be considered a finding item template, even if the finding item criteria are not stored in a single file or associated in other manners.

In some embodiments, a finding items template is generated in response to selection (either automatic or manual) of a report template for a particular medical imaging exam. For example, each finding item in the report template is identified. Then, for each finding item, finding item criteria for that finding item is determined, such as based on a lookup in a table or other data structure. The finding item criteria associated with each finding item in the report template may then be stored as a finding item template.

In some embodiments, each exam type is associated with a finding item template. In some examples, an exam type may be associated with multiple finding item templates and/or multiple exam types may be associated with a same finding item template. In some examples, the finding item(s) associated with an exam may be stored data linked to an exam and not stored in a single document or file. In some examples, a finding item template is generated to include certain finding items. For example, a finding item template may be generated based on various attributes related to the exam (such as body region, patient age, use of contrast material, imaging modality or combination thereof) to include only those finding items that are relevant to those attributes. The attributes related to the example may also be used when a report is generated. While the exact embodiment may vary as described above, an exam is associated with a listing (or identifiers) of finding items that can come from one or more templates linked to the exam or from data linked to the exam. For example, finding items associated with a chest x-ray may include LUNGS, HEART, MEDIASTINUM, PLEURA, BONES, TUBES/LINES, and UPPER ABDOMEN. Such finding items may be associated with anatomical regions or other classifications. The finding items may vary depending on a user's preferences or attributes of the user. Each finding item may be associated with default report content. For example, the LUNG finding items may be associated with "No pneumonia, mass, or other abnormality."

Each finding item may be associated with a "finding item criteria," which is usable to identify finding items that should be associated with the particular finding item (e.g., in addition to the default report content for that finding item or changes to the default report content). In some embodiments, finding item criteria may include a matching algorithm configured to identify text that is associated with that particular finding item. A matching algorithm may include character strings, keyword terms, searching rules, and/or artificial intelligence algorithms configured to identify text matching the concept of the finding item. For example, a matching algorithm for a lungs finding item may include letter combinations (e.g., word parts, words, phrases, etc. with regular expressions) that identify certain terms or combinations of terms in text. In some embodiments, a matching algorithm for identifying text associated with a particular finding item may be updated in response to manual association of text to a finding item. A "finding item template" as used herein may include a template for an actual medical report, e.g., including fields for portions of an actual medical report, such as title, medical practitioner information, patient information, default finding item text, etc., along with formatting parameters for the medical report. However, a "finding item template" may also refer to a set of data associated with the report, such as data associating finding items with associated finding item criteria. Thus, a finding item template may be a list, table, text file, database, and/or any other data format.

Figure 3A:
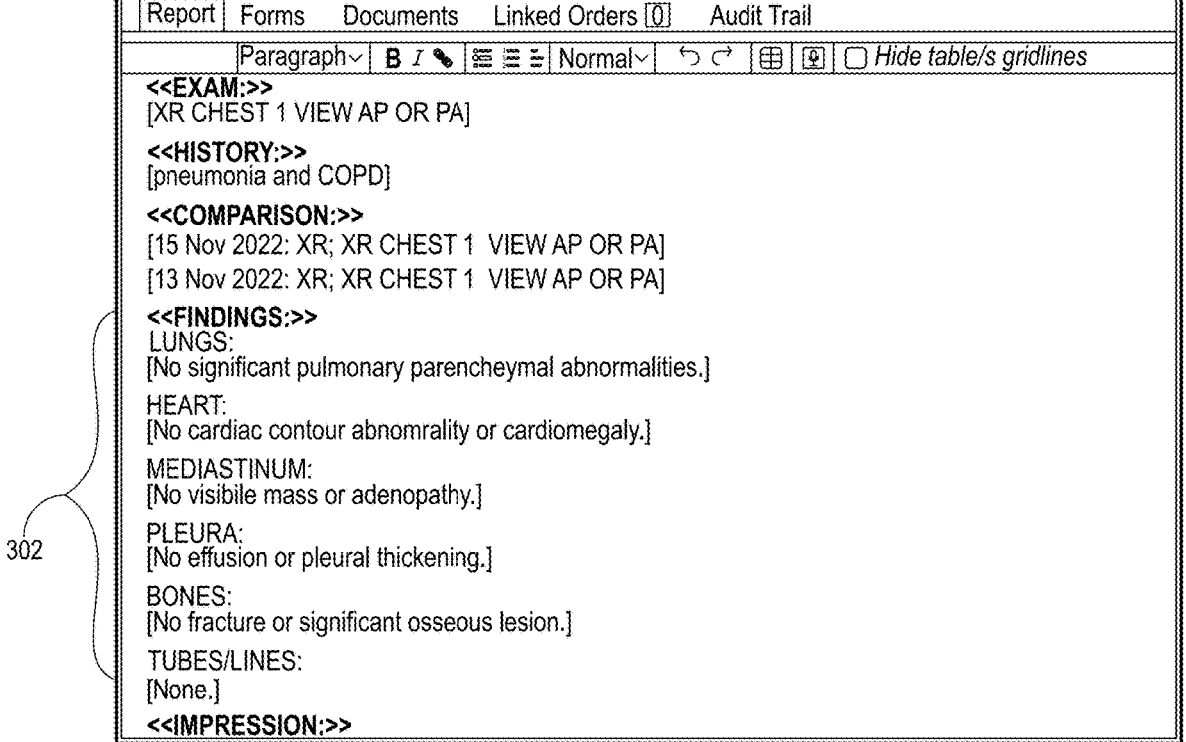
FIG. 3A illustrates an example user interface showing finding items 302 that are included in a template for a chest x-ray exam.

At block 208, the finding items may be displayed to the user, such as in a user interface. FIG. 3A illustrates an example user interface showing finding items 302 that are included in a template for a chest x-ray exam. As shown, each of the finding items 302 is pre-populated with template text that is associated with no findings (e.g., indicating nothing outside of the ordinary) for that particular finding item. As noted above, the speech organization functionality discussed herein may be applicable to report or document generation of any kind, including uses both inside and outside of the medical imaging field. Thus, while certain example herein refer to diagnostic medical imaging, the speech organization functionality, such as may be performed by the speech organization module 175 (FIG. 1), are also applicable to generation of laboratory, medicine, pathology, and/or other reports. As another example, FIG. 3B illustrates an example user interface of a laboratory report for a clinical chemistry workflow. In this example, each of the finding items 304 is pre-populated with template text that is associated with no findings (or "Normal") for the particular finding item. As discussed herein, text for respective finding items may be auto categorized to a finding item and/or auto populated into the report using the speech organization functionality discussed herein.

At block 210, the system receives text input from a user, such as via voice to text input or text entry via a keyboard or other input device. For example, the user may activate a voice recognition module that monitors input from a microphone of the system and converts the received speech into text. For example, the text input box 402A in FIG. 4 may be displayed responsive to the user selecting a voice to text function. In this example, a user has spoken the phrase "No significant parenchymal abnormality is seen in the right lower lobe. There is a nodule in the left lower lobe" and the system has implemented voice to text analysis and printed the text shown in text input box 402A. At this stage, the text in box 402A is not yet associated with a particular finding item.

In some embodiments, the input text is parsed into "phrases" of one or more words that identify a concept, and the phrases will then be processed by the categorization model for a possible association with a finding item. In some embodiments, parsing may be performed after matching of a character string by a matching algorithm to determine if additional characters or words should be grouped into a phrase any matched to a corresponding finding item. In some embodiments, the parsing is performed based on presence of a delimiter, such as a period, comma, or semicolon, that separates phrases from one another. In some embodiments, phrases may be determined based on a language model, such as a large language model, that is provided with input text and instructed to parse the input text into phrases. In other embodiments, input text may be parsed into phrases using other logic, such as a natural language processing library that provides sentence tokenization capabilities, part of speech tagging, topic modeling (e.g., Latent Dirichlet Allocation), n-gram analysis, and/or any other suitable algorithm.

Moving to block 212, a categorization model is applied to the received text to determine an associated finding item. For example, the categorization model may include a matching algorithm associated with each finding item in the selected template. Thus, in the example of FIG. 3, the template includes six finding items so the categorization model may only use matching algorithms associated with those specific six finding items, rather than to all of the possible finding items that could be included in report, such as tens, hundreds, thousands, or more finding items. In this way, the categorization model may more quickly and accurately associate text (e.g., phrases within the text) with the correct and relevant finding item.

In some implementations, the text provided by the user is analyzed as it is received, without further user input. For example, after each word, number of characters, phrase, sentence, or other amount of text is received by the system, the categorization model may be applied to the received text to identify a most likely associated finding item. In some embodiments, the matching algorithm for each of the finding items is applied to the text and outputs a confidence level that the text is associated with the particular finding item. For example, with the six finding items in FIG. 2, the six matching algorithms may include six sets of character strings that may be deterministically identified within text. In another example, the matching algorithms of finding items may confidence levels associated with those finding items, each indicating a likelihood that the text is associated with the respective finding item. Then, a finding item with the highest confidence level may be associated with the text. Returning to the example of FIG. 4, the categorization model may automatically determine that the text in box 402A is associated with the Lungs finding item and, accordingly, may update the text input as shown in 402B to include the "LUNGS:" heading above the spoken text.

Next, at block 214, the system determines whether a finding item associated with the text has been identified, such as at a threshold confidence level. In some examples, a highest confidence level for a finding item may cause selection of that finding item as the associated finding item. The example confidence levels below represent example confidence levels for each of seven finding items that are calculated based on a particular text, such as provided by the user via speech to text. In this example, the highest confidence level is associated with the Lungs, so in a system where the highest confidence level is determined as the matching finding item, the particular text would be associated with the lungs finding item. In other examples, the confidence level must be greater than a predetermined threshold for an input text to be assigned to the finding item. For example, if the threshold confidence level was 90%, the confidence levels in the table below would be inconclusive since the highest confidence level was 85% for the lungs finding item. In another example, if a highest finding item confidence level is near another finding item confidence level, e.g., within a predetermined minimum, such as 5 percentage points, the categorization model may return an inconclusive output indicating that the text has not been associated with a particular finding item. In other examples, the selection of a finding item based on a categorization model may be performed in other manners, such as some combination of the rules noted above.

| Finding Item | Confidence Level |
|---|---|
| Lungs | 85 |
| Heart | 45 |
| Mediastinum | 30 |
| Pleura | 80 |
| Bones | 5 |
| Tubes/Lines | 10 |
| Upper Abdomen | 65 |

If at block 214 an associated finding item has been identified, the method continues to block 216 where the text is associated with the finding item. This association may be immediately displayed in a user interface, such as is shown with reference to the update to include the "LUNGS" finding item in text box 402B after the categorization model has automatically associated the input text with the lungs finding item. In some embodiments, the association of the text with a finding item may be automatically added to a report, e.g., to the report illustrated in FIG. 3. In some examples, the input text may be added to a report when the user selects a submit button 403, such as after reviewing the added finding item for accuracy.

If, however, at block 214, an associated finding item is not identified (e.g., if a confidence level of an association between the input text and each of the finding items in the template is less than a threshold), the method continues to block 218 where additional rules, e.g., deterministic rules, may be evaluated to identify a corresponding finding item to which the input text should be assigned. One example of a rule may indicate that for input text that is not automatically matched to a finding item by a matching algorithm is associated with the last matched finding item. Thus, text that is not matched with a particular finding item at block 212 may be automatically assigned to a previously matched finding item. Another example rule may indicate that input text that is not automatically matched to a finding item may cause an alert or prompt to be provided to the user to allow the user to select the appropriate finding item. Another example rule may indicate that if the unmatched text is the first text (e.g., first text received for a particular report), the system associates the text with the OTHER finding item. In some examples, a drop-down menu and/or other selection interface may be provided to the user, such as displaying only a few of the finding items having the highest confidence levels. In other examples, other rules, such as may be organized in a hierarchical manner, may be generated by the system and/or the user to allow for more comprehensive association of input text to finding items. In some examples, to create a new finding item that is not in the template, the text that is dictated or reported may preceded a colon punctuation. For example, if BRAIN: appears, the system will associate the next dictated sentence or phrase to a new finding item called BRAIN.

Once a rule has identified the appropriate finding item for an input text, the method continues to block 220 where the text is associated with the finding item according to the rule.

At block 222, the system determines whether additional text input is to be received from the user. In some examples, this determination may be automatic, such as based on completeness of the report. In some examples, this determination may be based on user input indicating whether or not additional text input will be provided.

At block 224, a report, including the finding items of the selected template, is pre-populated with text associated with finding items properly placed within the finding items in the report.

In some examples, the system may provide additional functionality to the user, such as to allow the user to add a new finding item to a report (e.g., that was not included in the report template selected for the medical imaging exam). For example, the user may provide input text indicating an additional finding item, such as through the use of a particular format of text, e.g., all-caps text followed by a colon, that is automatically detected by the system because the generation of a new finding item in the report. In some embodiments, text associated with a finding item may be reassigned to another finding item based on input from the user. For example, if finding item text is initially associated with a "Lungs" finding item, e.g., based on matching of a character string in the "Lungs" finding item criteria to characters in the finding item text, but the user determines that the finding item text is more appropriately associated with a "heart" finding item, the user may indicate the change. For example, the system may provide a drag-and-drop functionality that allows the user to select the finding item text and drag the finding item text onto an area associated with the desired finding item. In other embodiments, other user interface functionality (e.g., a drop-down listing of other finding items in the finding item template, such as responsive to a right-click on the particular finding item text that is to be moved) may be provided to allow the user to indicate a change of particular finding item text from one finding item to another. In some embodiments, if a finding item text is moved from one category to another, a notification is provided to the user (e.g., an administrative user) indicating that the finding item criteria for one or both of those finding items may need to be updated. In some embodiments, in this circumstance, the system may automatically make changes to the finding item criteria, possibly after proposing a change of the finding item criteria to the user and receiving authorization from the user.

Example Finding Item Template Generation

In some embodiments, finding item templates associated with medical imaging exams of particular types (and/or other criteria) may be generated based on analysis of reports associated with medical imaging exams. For example, generation of a finding item template for a particular type of medical imaging exam may be generated based on analysis of a collection of reports associated with that type of medical imaging exam. For example, finding item criteria for particular finding items may be automatically generated based on analysis of finding item text associated with the particular finding items in the collection of reports. The report and images may be redacted so long as there remains a way to associate the report with the corresponding exam. The reports may be in various formats.

A finding item template may be created and associated with each exam type. The finding item template may include a list of finding items, that includes the categories of data one desires to collect. For example, for a Chest Radiograph, finding indications (e.g., findings vs no findings) in various regions, such as the LUNGS, MEDIASTINUM, HEART, BONES, PLEURA, TUBES/LINES, OTHER, may be included in a finding item template to enable data collection for such finding items. In some embodiments, the finding item criteria associated with the determined finding items may be automatically created and associated with finding items such that the speech organization module may categorize text phrases (e.g., related groups of words or sentences) in other report examination text (e.g., text dictated by a radiologist or included in a medical report) as being associated with particular finding items.

As an example, a finding section of a report may be accessed by the speech organization module to parse the text into phrases that may then each be associated with a most relevant finding item. In some implementations, a phrase may be categorized with an "OTHER" finding item if it does not match any of the finding item criteria in the finding item template. Although character strings are discussed as one form of a finding item criteria, finding item criteria may use natural language processing with AI, an LLM, and/or other more automated approaches as an alternative to, or in addition to, character strings.

In some embodiments, natural language processing may then be used to determine a finding indication (e.g., whether the finding item text describes a finding or no finding) based on the finding item text. For example, each finding item may be classified as either FINDING or NO FINDING.

In some embodiments, the finding item indications associated with an exam may be used to generate a model and/or train an algorithm to automatically predict finding items associated with medical images.

Example Speech Organization

Figures 5A, 5B:
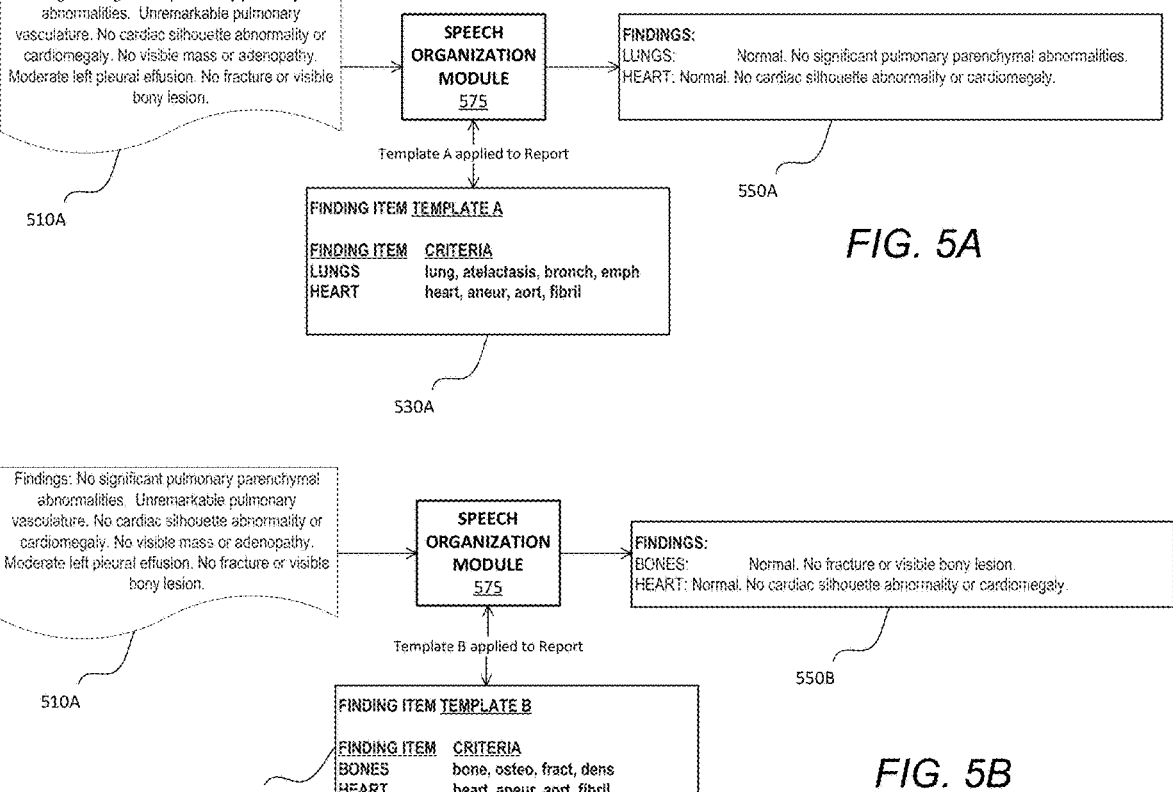
FIG. 5 (including FIGS. 5A, 5B, and 5C) illustrate example implementations of a speech organization module, which may provide the same or similar functionality as speech organization module of FIG. 1.

FIG. 5 (including FIGS. 5A, 5B, and 5C) illustrate example implementations of a speech organization module 575, which may provide the same or similar functionality as speech organization module 175 (FIG. 1), such as in the context of a computing system or cloud computing environment. In the examples of FIG. 5, an example input text is accessed by the speech organization module 575, which applies a finding item template and outputs a report fragment including phrases from the input text that are categorized into the appropriate finding items (e.g., categories) within the report.

In the example of FIG. 5A, the input text 510A includes a text blurb, or free-form text, such as may be dictated or written by a radiologist or other medical professional. In this example, the input text 510A does not include associations with finding items. The finding item template A 530A has been selected by a user to perform categorization of input text into finding items. For example, a user may select a finding item template that includes only those finding items that are of importance for a particular project. Similarly, a user may select finding item criteria for particular finding items, such as to customize portions of the input text (generally referred to as "phrases" of the input text) that may be associated with respective finding items. In some embodiments, a finding item template is associated with an individual, a group of individuals, an organization, or one or more computing systems, such that a finding item template is automatically selected as a default based on these factors.

In the example of FIG. 5A, a finding item template A 530A includes two finding items: lungs and heart, each with associated finding item criteria. In this example, the finding item criteria are character strings, but in other embodiments other types of finding item criteria may be used. As shown in FIG. 5A, as the finding item template A 530A is applied to the input text 510A, a report fragment 550A is provided as an output, with phrases from the input text that matched the lungs finding item criteria associated with the lungs finding item and phrases within the input text matching the heart finding item criteria associated with the heart finding item. In this example, not all of the input text 510 has been categorized as related to one of the finding items in the template A. In some embodiments, additional input text that is not categorized based on the template may be categorized into an "Other" category or the like.

FIG. 5B illustrates the same input text 510A being accessed by the speech organization module 575, but now in the evaluation of finding item template B 530B (rather than finding item template A 530A as in FIG. 5A). In this example, finding item template B 530B includes two finding items: bones and heart, each with associated finding item criteria, which are character strings in this example. When the speech organization module 575 evaluates the report text 510A with reference to the finding item template B 530B, the report fragment 550B includes phrases from the input text matching finding item criteria for the bones finding item associated with bones and phrases matching finding item criteria associated with the heart finding item associated with the heart. Other portions of the report text that did not match finding item criteria for bones or heart are not included in the report fragment (although in other embodiments the nonmatching text and/or phrases may be included in and "other" category or the like).

FIG. 5C illustrates an example where a medical report is processed by the speech organization module 575 based on the same finding item template A 530A that was used in FIG. 5A. Here, though, the input text 510C already includes finding items and associated finding item text. In some embodiments, the speech organization module 575 is configured to disregard finding item associations of text in the input text 510C, such that certain phrases of the input text 510C may be associated with different finding items in the report fragment 550C and the input text 510C. For example, in some embodiments a finding item template may include a higher-level finding item than what is included in an input text. For example, a finding item template may include a finding item for "Chest" that generally includes finding items that might be related to multiple other finding items in other reports, such as "lungs", "heart", and "mediastinum." Thus, through the use of the speech organization module 575 and a user-selected template (template A 530A in the example of FIG. 5C), an existing medical report may be smartly re-organized to provide the appropriate finding item text for each of the finding items in the template.

Example Model Development

Figure 6:
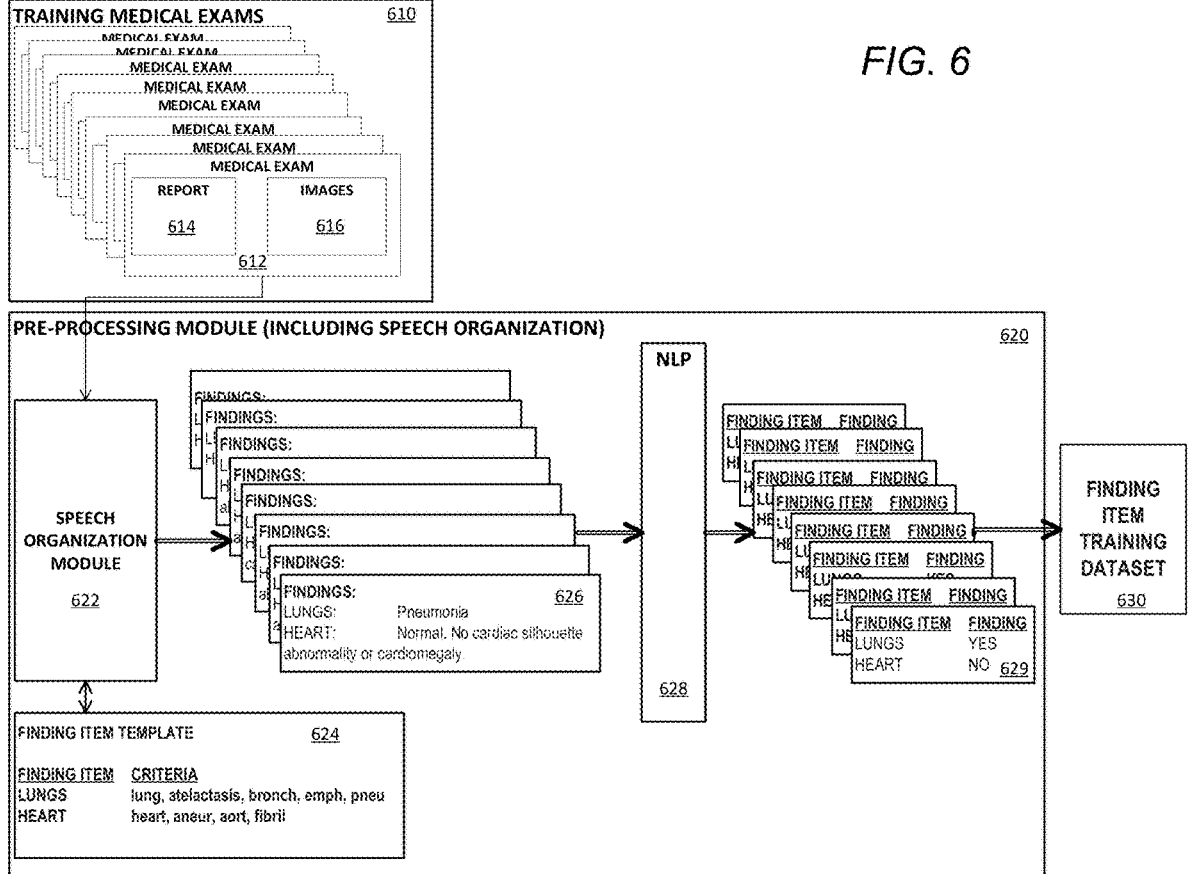
FIG. 6 is a block diagram illustrating one example of components and a method of generating a model for identifying anomalies (or any other feature that can be detected)

FIG. 6 is a block diagram illustrating one example of components and a method of generating a model for identifying anomalies (or any other feature that can be detected) in medical images based on training data that has been organized using the speech organization systems and methods discussed above. In some embodiments, the components of FIG. 6 are included in and/or performed by the computing system 150. In other embodiments, another computing system (e.g., a cloud-based system) may include and/or perform operations associated with the components illustrated in FIG. 6.

As shown in the example of FIG. 6, the output from the preprocessing module 620 is a finding item training data set (or simply "training data set"). As shown in FIG. 7, this training data set is then used to train a neural network 720 and output an image classification model 730 that is usable by an inference module 750. The inference module 750 may then access medical images 702 (that have not been analyzed by a human reader) and generate classifications of finding item text (e.g., normal or abnormal) associated with the medical image 702 without requiring any human review of the medical image 702. In general, the various components and modules illustrated in FIGS. 6 and 7 may be distributed across multiple devices and/or included within a single device.

FIG. 6 illustrates a set of training medical exams 610 that have been selected for use in training a neural network and creation of a corresponding image classification model. In this example, each of the medical exams 612 includes a medical imaging report 614 and one or more corresponding medical images 616. The report 614 may be in various formats, such as a text blurb (e.g., one or more phrases or sentences that are not categorized) or in a more structured format, such as with text associated with finding items or other sections identified in the report. The images may be any type of medical image, such as from any medical imaging equipment discussed herein (e.g., see FIG. 1). The findings, classifications, descriptions, etc. indicated in the report 614 describes anatomical features included in the corresponding medical exam images 616. Because the training medical exams 610 are used to train a neural network and generate an image classification model, selection of the medical exams 612 to include in the training medical exams 610 may be performed in various manners to optimize the set of training medical exams 610. For example, if Hospital A specializes in identification and/or treatment of brain tumors (or particular brain tumors), medical exams 612 with reports 614 prepared by Hospital A personnel may be a good choice for use as the training medical exams 610 for generation of an image classification model that is usable to identify brain tumors (at Hospital A or anywhere else that the image classification model is made available). In this example, the image classification model that is generated based on this training medical exams 610 may provide finding item data (e.g., finding item text and categorization of the finding item text as normal or abnormal) that mirrors finding item data that would be obtained by analysis of a medical image by a member of Hospital A. In a similar manner, the training medical exams 610 may be selected based on one or more particular anatomical regions or exam types (e.g., head CTs), characteristics of the reading operators (e.g., an individual or group of users with a medical specialty), and/or other characteristics of the medical exams.

A preprocessing module 620 uses speech organization, as discussed above with reference to FIGS. 2-5, and natural language processing to generate a finding item training data set 630 representative of the training medical exams 610. Initially, the speech organization module 622 selects a finding item template 624 to use in organizing report text (in each of the reports 614 of the training medical exams 610). In the example of FIG. 6, a finding item template 624 includes two finding items (LUNGS and HEART) and finding item criteria associated with each of those finding items. In this example, the finding item criteria are character strings (e.g., combinations of letters) that may be found in a text phrase of the report to cause categorization of that particular text phrase with the finding item. For example, if a phrase of report text includes "lung", that report text may be categorized and associated with the lungs finding item. As noted above, the finding item criteria may include rules, algorithms, regular expressions, etc. that are usable to categorize words or phrases of report text with particular finding items. In this example, only two finding items are included in the finding item template 624 for ease of description. Any number of finding items (and associated criteria) may be included in a finding item template. In some embodiments, a user of the system selects the finding item template 624 from a set of available finding item templates. In some embodiments, the user may generate a new finding item template 624. In some embodiments, the system may automatically select a finding item template 624 based on characteristics of the training medical exams 610, for example.

The speech organization module 622 may then apply the finding item template 624 to each report 614 to identify report text (e.g., words or phrases) that should be assigned to particular finding items. Advantageously, regardless of the format of the reports 614, the re-categorized findings 626 are in the same format and report text is categorized based on the same criteria for all of the reports 614. Thus, even if the training medical exams 610 includes reports 614 in different formats, such as some reports in a text blurb format (e.g., one or two sentences that are dictated by a radiologist), and some reports are in a categorized format (e.g., anatomical sections with associated text), the speech organization module 622 provides a normalization or standardization of findings from the various report formats. In the example of FIG. 6, the recategorized findings 626 show "pneumonia" report text has been associated with the LUNGS finding item (e.g., based on matching with the character string "pneu" in the finding item criteria associated with LUNGS) and "Normal. No cardiac silhouette abnormality or cardiomegaly" report text has been associated with the HEART finding item.

Next, the natural language processing module 628 (or NLP 628) analyzes the finding item text associated with finding items and generates a classification for the finding item, such as an indication of whether or not a finding (e.g., anything other than normal) is indicated by the finding item text. For example, the re-categorized findings 626 result in a findings data 629 indicating that there was a finding associated with the LUNGS finding item and there was not a finding associated with the HEART finding item. As discussed elsewhere herein, classification (e.g., the finding indication) associated with each finding item by the NLP 628 may vary from case to case. In some examples, the user selects the available/possible findings that the NLP 628 should identify in re-categorized findings 626 for each of the medical exams 612. For example, in the example of FIG. 6, a user may have indicated that a finding of "YES" or "NO" should be assigned to each of the finding items by the NLP 628. In other embodiments, the findings that are generated by the NLP 628 may be more descriptive, such as describing characteristics of a particular finding (or non-finding).

The combination of the findings data 629 for each of the medical exams 612 collectively comprises the training data set 630 that will be used to train an AI system. In some embodiments, the training data set 630 organizes the findings data 629 in a table format, such as with a first column identifying the particular medical exam 612, a second column identifying the finding item, and the third column identifying the specific finding generated by the NLP 628. Thus, the finding item training data set 630 may comprise a concise set of information summarizing findings for finding items in the finding item template 624. In other embodiments, the training data set 630 may be organized and/or formatted in any other manner. In some embodiments, the training data set 630 may include links to and/or portions or all of the associated reports 614 and images 616 for each of the findings data 629.

Moving to FIG. 7, with the training data set 630 generated, the model generation module 180 may train a neural network 720 (based on the training data set 630), which outputs an image classification model 730. For example, the neural network may be trained to identify associations between features in medical images and findings classifications. As one example, if a finding item training data set includes a "YES" or "NO" finding for a "Lungs" finding item for each of 500 medical exam, the neural network may identify common positive features or characteristics of medical images with a "YES" classification (e.g., 212 of the 500 medical exams) and common negative features or characteristics of medical images with a "NO" classification (e.g., the remaining 288 of the 500 medical exams). The image classification model 730 that is output by the neural network 720 includes logic that identifies whether a medical image includes the positive and/or negative features or characteristics and provides an automated classification (e.g., "YES" or "NO") for the LUNGS finding item that may be used on other similar medical images based on that logic.

In some embodiments, the weights and biases associated with training of the neural network may be adjusted by a user and/or automatically adjusted by the model generation module 180.

The training process for a neural network is explained in detail in many scholarly works, but in general the neural network makes a guess as to the classifications (e.g., for the LUNGS and HEART finding items) for a particular medical image of the training data set 630. Then, the neural network checks to see if the guess was correct. A loss function may then be calculated to indicate how far off the neural network's guess was from the actual finding (in the training data set 630). This loss function may then be used to adjust internal settings of the neural network, such as weights and/or biases, based on the calculated loss function. As more images are analyzed in this way, the loss function may be reduced and the neural network becomes better at predicting classifications correctly.

The inference module 750 is configured to apply the image classification model 730 to medical images 702 to generate finding items data 740 that includes a predicted finding (e.g., normal or abnormal) for each of the finding items. The medical image 702 may be a new medical image that was just acquired from a medical imaging device. Alternatively, the medical image 702 may be accessed from any other source.

Advantageously, inference module 750 outputs findings items data 740 that includes a predicted finding for each of the finding items in the finding item template 624 that was used to generate the training data set 630. In this example, as shown in FIG. 6, the finding items template 624 includes two finding items. Thus, the image classification model 730 is configured to output a classification (e.g., a "Yes" or a "No") for each of the two finding items based on analysis of the medical image 702, without any previous analysis or input from human user's and/or other automated analysis systems. In some embodiments, the finding items data 740 include the confidence levels associated with each of the predicted findings. For example, a confidence level between zero (no confidence) and 100 (or some other range) may be included in the finding items data 740. As an example, the finding items data associated with the medical image 702 may include:

| Finding item | Finding | Confidence level |
| --- | --- | --- |
| LUNGS | YES | 82 |
| HEART | NO | 90 |

These example findings indicate that the image classification model 730 was 82% confident in the YES finding for the LUNGS finding item and 90% confident in the NO finding for the HEART finding item. In some embodiments, the threshold confidence level to provide a YES or NO classification for a finding item (or other classification, as discussed herein) may vary, such as by user selection of the threshold. For example, if the confidence level for a YES finding is set to 90%, the YES finding in the table above would be changed to a NO finding (even though the confidence level of 82 may be considered very high for this type of analysis).

In the embodiment of FIG. 7, a report generation module 185 receives the finding items data 740 and generates a medical report 760 based on a report template 752. The report generation module 185 may include default text for each of the finding items, such as based on whether or not a finding was indicated for the finding item. The report template 752 two may also indicate formatting and/or patient, exam, physician, or other information to include in the medical report 760. In some embodiments, report generation module 185 may access a medical data information system, such as a patient database of a hospital, to obtain information for the medical report 760.

In this example, the feedback module 770 may be provided with user feedback on accuracy of the predicted findings that are included in the medical report 760. For example, if the reviewing doctor discovers that the YES finding for the LUNGS finding item in the case discussed above is not accurate, the doctor may access a feedback user interface to indicate the incorrect finding. The feedback module 770 may then send feedback information as fine-tuning data 772 that may periodically be used by the model generation module 180 to update the training of the neural network and, therefore generate an updated image classification model 730 that presumably would not make the same types of misclassifications.

Thus, the inference module 750, which may operate on a separate device, such as a computer at a hospital that receives medical images from medical imaging equipment, may generate medial reports that include findings determined by AI in a similar manner as findings were identified by reporters of the reports in the training medical exams 610.

Example Implementations

Examples of the implementations of the present disclosure can be described in view of the following example clauses. The features recited in the below example implementations can be combined with additional features disclosed herein. Furthermore, additional inventive combinations of features are disclosed herein, which are not specifically recited in the below example implementations, and which do not include the same features as the specific implementations below. For sake of brevity, the below example implementations do not identify every inventive aspect of this disclosure. The below example implementations are not intended to identify key features or essential features of any subject matter described herein. Any of the example clauses below, or any features of the example clauses, can be combined with any one or more other example clauses, or features of the example clauses or other features of the present disclosure.

Clause 1. A computerized method, performed by a computing system having one or more hardware computer processors and one or more non-transitory computer readable storage device storing software instructions executable by the computing system to perform the computerized method comprising: determining a set of training medical imaging exams each including a training report and a training medical image; determining one or more finding items and associated finding item criteria; for each of the training medical imaging exams: use the finding item criteria to reorganize text of the training report into a list of finding items, each associated with text extracted from the training report text; use natural language processing to analyze the resultant text associated with each finding item to determine an associated classification of each finding item; and store, in a training dataset, the training medical imaging exam, the associated finding items, the matching text, and the classifications resulting from the analysis of the matching text; and training a neural network using the training dataset, wherein the neural network learns to output, for other medical imaging exams, one or more finding items and an associated classification data.

Clause 2. The computerized method of clause 1, wherein the classifications are one or more of: positive or negative, improved or worse, observation or recommendation, or more specific classifications.

Clause 3. A computerized method, performed by a computing system having one or more hardware computer processors and one or more non-transitory computer readable storage device storing software instructions executable by the computing system to perform the computerized method comprising: determining a set of training medical imaging exams each including a training report and a training medical image; determining one or more finding items and associated finding item criteria in a finding item template; for each of the training medical exams: for each of the finding items in the finding item template: applying the associated finding item criteria to text of the training report to identify any matching text; analyzing the matching text associated with the finding item to generate a finding item indication indicating whether the matching text indicates a finding or no finding; and storing, in a training dataset, an association between the training medical exam, the finding items, the matching text for each finding item, and the finding item indication for each finding item; training a neural network using the training dataset, wherein the neural network learns to predict finding item indications of medical images not included in the set of training medical exams; and outputting a trained image classification model configured to predict features of medical images based on learned relationships between the training medical images and the associated finding item indications.

Clause 4. The computerized method of clause 3, further comprising: associating the predicted finding item indications and associated finding items with the training medical exam.

Clause 5. The computerized method of clause 3, further comprising: receiving access to a new medical image not included in the set of training medical exams; applying the trained image classification model to the new medical image to predict finding item indications for each of the finding items; and providing the predicted finding item indications and associated finding items for use in a medical report.

Clause 6. The computerized method of clause 5, wherein the new medical image is sourced in near real-time from a medical imaging device and the predicted finding item indications and associated finding items are provided in near real-time to assist in patient diagnosis or treatment.

Clause 7. The computerized method of clause 5, updating electronic medical records of a patient to include the predicted finding item indications and associated finding items.

Clause 8. The computerized method of clause 5, further comprising: accessing a report template associated with a user; and based on the report template and the predicted finding item indications, generate a medical report.

Clause 9. The computerized method of clause 8, wherein the report template indicates one or more of: content, formatting, or order of content of a medical report.

Clause 10. The computerized method of clause 5, further comprising: receiving feedback from a reviewer of the predicted finding item indications and associated finding items; and initiating fine-tuning of the image classification model based on the received feedback to improve one or more of accuracy and relevance of predictions from the image classification model.

Clause 11. The computerized method of clause 3, wherein the set of training medical exams are selected based on one or more: exam criteria or radiologist criteria.

Clause 12. The computerized method of clause 11, wherein the radiologist criteria indicate one or more of: a particular radiologist or radiologist group.

Clause 13. The computerized method of clause 3, further comprising: adjusting one or more of weights or biases of the neural network during the training process using optimization algorithms to minimize prediction error.

Clause 14. The computerized method of clause 3, further comprising: normalizing each of the training medical images by applying transformations including one or more of rotations, scaling, or translations.

Clause 15. A computerized method, performed by a computing system having one or more hardware computer processors and one or more non-transitory computer readable storage device storing software instructions executable by the computing system to perform the computerized method comprising: determining a type of a medical imaging exam; determining a finding item template associated with the determined type of medical imaging exam, wherein each of a plurality of finding item templates includes different sets of one or more finding items and associated finding item criteria; receiving text input from a user of the computing system; for each phrase in the text input, applying a categorization model configured to evaluate the finding item criteria of the determined finding item template with reference to the phrase, wherein the categorization model provides a matching finding item for each phrase, based on likelihoods of the phrase matching with particular finding items, and not other finding items that are not included in the determined finding item template; and associating the phrase to a matching finding item; and automatically updating a report to include the phrases associated with the matching finding items.

Clause 16. The computerized method of clause 15, wherein each of the finding item criteria includes a character string or rule for identifying phrases that should be associated with the corresponding finding item.

Clause 17. The computerized method of clause 15, wherein each of the finding item criteria comprises an artificial intelligence model configured to identify phrases conceptually associated with the corresponding finding item.

Clause 18. The computerized method of clause 17, wherein the artificial intelligence model comprises one or more large language model.

Clause 19. The computerized method of clause 15, wherein the determined finding item template includes a list of finding items and a corresponding list of finding item criteria.

Clause 20. The computerized method of clause 15, wherein matching finding items are determined based on confidence levels that the phrase matches respective finding items.

Clause 21. The computerized method of clause 20, wherein a finding item with a highest confidence level is selected as the matching finding item.

Clause 22. The computerized method of clause 15, wherein the categorization model further includes one or more deterministic rules configured to associate a phrase with a finding item.

Clause 23. The computerized method of clause 22, wherein the deterministic rules are evaluated in response to unsuccessfully identifying a matching finding item based on the finding item criteria.

Clause 24. The computerized method of clause 15, wherein the text input is parsed into phrases by a large language model.

Clause 25. A computerized method, performed by a computing system having one or more hardware computer processors and one or more non-transitory computer readable storage device storing software instructions executable by the computing system to perform the computerized method comprising: determining one or more attributes of a medical imaging exam; generating a finding item template including one or more finding items associated with the one or more attributes of the medical imaging exam, wherein each of the one or more finding items is associated with corresponding finding item criteria; receiving text input from a user of the computing system; for each phrase in the text input, applying a categorization model configured to evaluate the finding item criteria of the determined finding item template with reference to the phrase, wherein the categorization model provides a matching finding item for each phrase; and associating the phrase to a matching finding item; and automatically updating a report to include the phrases associated with the matching finding items.

Clause 26. The computerized method of clause 25, wherein the one or more attributes of the medical imaging exam are the finding items in a report template.

Clause 27. The computerized method of clause 26, wherein the report template is automatically selected based on an exam type.

Clause 28. The computerized method of clause 26, wherein the report template includes default text for one or more of the finding items.

Clause 29. The computerized method of clause 26, further comprising: generating a report based on the report template, including each of the finding items in the report template and any matching text associated with respective finding items as determined by the categorization model.

Clause 30. The computerized method of clause 29, wherein the report includes default text associated with one or more of the finding items.

Clause 31. The computerized method of clause 26, further comprising: generating a conclusion or recommendation based at least one the matching text associated with the finding items, wherein the conclusion or recommendation includes at least some of the matching text.

Clause 32. The computerized method of clause 25, wherein the finding items are further determined based on one or more user, user attribute, system, or system attribute.

Clause 33. The computerized method of clause 25, wherein the categorization model is configured to compare text input with only those finding item criteria of the finding item template, and not compare text input with finding item criteria of a plurality of other finding items that are not included in the finding item template.

Clause 34. The computerized method of clause 25, wherein a first finding item criteria associated with a first finding item includes one or more character strings.

Clause 35. The computerized method of clause 25, further comprising: generating a user interface configured to receive user input updating first finding item criteria associated with a first finding item.

Clause 36. The computerized method of clause 25, wherein the first finding item criteria includes one or more character strings and the update indicates one or more of: removal of one or more of the character strings, modification of one or more of the character strings, or addition of a new character string.

Additional Implementation Details and Embodiments

Various embodiments of the present disclosure may be a system, a method, and/or a computer program product at any possible technical detail level of integration. The computer program product may include a computer readable storage medium (or mediums) having computer readable program instructions thereon for causing processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid-state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid-state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

As described above, in various embodiments certain functionality may be accessible by a user through a web-based viewer (such as a web browser), or other suitable software program. In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments may not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computing system comprising:
a hardware computer processor;
a non-transitory computer readable medium having software instructions stored thereon, the software instructions executable by the hardware computer processor to cause the computing system to perform operations comprising:
determining a set of training medical imaging exams each including a training report and a training medical image;
determining one or more finding items and associated finding item criteria in a finding item template;
for each of the training medical exams:
for each of the finding items in the finding item template:
applying the associated finding item criteria to text of the training report to identify any matching text;

analyzing, using natural language processing, the matching text associated with the finding item to generate a finding item indication indicating whether the matching text indicates a finding or no finding; and storing, in a training dataset, an association between the training medical exam, the finding items, the matching text for each finding item, and the finding item indication for each finding item;

executing a neural network on the training dataset, wherein the neural network is configured to:

identify, for each finding item indication, patterns among training medical images associated with that specific finding item indication;

iteratively adjust internal parameters, including weights and biases, using a loss function that quantifies prediction error between output of the neural network and the actual finding item indications in the training dataset and output an image classification model that encodes learned relationships between visual features of the training medical images and the associated finding item indications;

wherein the image classification model is configured to:

receive as input a medical image not included in the training dataset;

analyze the medical image to generate, for each finding item, a predicted finding item indication and an associated confidence level; and provide the predicted finding item indications for use in generating a medical report or updating an electronic medical record of the patient.

2. The computing system of claim 1, wherein the operations further comprise:

associating the predicted finding item indications and associated finding items with the training medical exam.

3. A computerized method, performed by a computing system having one or more hardware computer processors and one or more non-transitory computer readable storage device storing software instructions executable by the computing system to perform the computerized method comprising:

determining a set of training medical imaging exams each including a training report and a training medical image;

determining one or more finding items and associated finding item criteria;

for each of the training medical imaging exams:

use the finding item criteria to reorganize text of the training report into a list of finding items, each associated with text extracted from the training report text;

use natural language processing to analyze the resultant text associated with each finding item to determine a finding item indication associated with each finding item; and store, in a training dataset, the training medical imaging exam, the associated finding items, the matching text, and the finding item indications resulting from the analysis of the matching text; and training a neural network using the training dataset, wherein the neural network learns to output, for other medical imaging exams, one or more finding items and associated finding item classifications based on analysis of respective medical imaging exams.

4. The computerized method of claim 1, wherein the finding item indications are one or more of: positive or negative, improved or worse, observation or recommendation, or more specific classifications.

5. A computerized method, performed by a computing system having one or more hardware computer processors and one or more non-transitory computer readable storage device storing software instructions executable by the computing system to perform the computerized method comprising:

determining a set of training medical imaging exams each including a training report and a training medical image;

determining one or more finding items and associated finding item criteria in a finding item template;

for each of the training medical exams:

for each of the finding items in the finding item template:

applying the associated finding item criteria to text of the training report to identify any matching text;

analyzing the matching text associated with the finding item to generate a finding item indication indicating whether the matching text indicates a finding or no finding; and storing, in a training dataset, an association between the training medical exam, the finding items, the matching text for each finding item, and the finding item indication for each finding item;

training a neural network using the training dataset, wherein the neural network learns to predict finding item indications of medical images not included in the set of training medical exams based on analysis of respective medical images; and outputting a trained image classification model configured to analyze features of medical images to predict finding item indications of the medical images based on learned relationships between the training medical images and the associated finding item indications.

6. The computerized method of claim 5, further comprising:

associating the predicted finding item indications and associated finding items with the training medical exam.

7. The computerized method of claim 5, further comprising:

receiving access to a new medical image not included in the set of training medical exams;

applying the trained image classification model to the new medical image to predict finding item indications for each of the finding items; and providing the predicted finding item indications and associated finding items for use in a medical report.

8. The computerized method of claim 7, wherein the new medical image is sourced in near real-time from a medical imaging device and the predicted finding item indications and associated finding items are provided in near real-time to assist in patient diagnosis or treatment.

9. The computerized method of claim 7, updating electronic medical records of a patient to include the predicted finding item indications and associated finding items.

10. The computerized method of claim 7, further comprising:

accessing a report template associated with a user; and based on the report template and the predicted finding item indications, generate a medical report.

11. The computerized method of claim 10, wherein the report template indicates one or more of: content, formatting, or order of content of a medical report.

12. The computerized method of claim 7, further comprising:

receiving feedback from a reviewer of the predicted finding item indications and associated finding items; and initiating fine-tuning of the image classification model based on the received feedback to improve one or more of accuracy and relevance of predictions from the image classification model.

13. The computerized method of claim 5, wherein the set of training medical exams are selected based on one or more: exam criteria or radiologist criteria.

14. The computerized method of claim 13, wherein the radiologist criteria indicate one or more of: a particular radiologist or radiologist group.

15. The computerized method of claim 5, further comprising:

adjusting one or more of weights or biases of the neural network during the training process using optimization algorithms to minimize prediction error.

16. The computerized method of claim 5, further comprising:

normalizing each of the training medical images by applying transformations including one or more of rotations, scaling, or translations.

* * * * *